United States Patent
Shugart

[19]

[11] Patent Number: 5,968,453
[45] Date of Patent: Oct. 19, 1999

[54] REAGENT CARTRIDGE

[75] Inventor: Phillip G. Shugart, Brea, Calif.

[73] Assignee: Carolina Liquid Chemistries Corporation, Brea, Calif.

[21] Appl. No.: 08/896,324

[22] Filed: Jul. 17, 1997

[51] Int. Cl.[6] .......................... B32B 27/04; B32B 27/12; B32B 5/02
[52] U.S. Cl. .......................... 422/102; 422/104; 206/569; 220/501; 220/524; 220/555
[58] Field of Search .............................. 422/64, 102, 104; 436/43, 49; 206/557, 569; 220/501, 523, 524, 553, 555

[56] References Cited

U.S. PATENT DOCUMENTS

| | | | |
|---|---|---|---|
| 4,634,576 | 1/1987 | Galle et al. | 422/102 |
| 5,352,413 | 10/1994 | Kratzer et al. | 422/100 |
| 5,462,715 | 10/1995 | Koch et al. | 422/64 |

*Primary Examiner*—Long V. Le
*Attorney, Agent, or Firm*—Robert R. Meads

[57] ABSTRACT

A single compartment, non-wedged shaped reagent cartridge for use in an automated clinical chemistry analyzer. The cartridge comprises a hollow relatively narrow reagent compartment formed by an axially elongated, bottom, an axially elongated top, a front end portion and a rear end portion extending vertically between the bottom and top and connecting to opposing right and left sidewalls for completing the reagent compartment. A shoulder engaging flange extends from the top for supporting the cartridge on a shoulder in a cartridge receiving carousel of an automated clinical analyzer including transfer probes for insertion into at least one opening in the top of the cartridge for fluid transfer into the clinical analyzer.

6 Claims, 2 Drawing Sheets

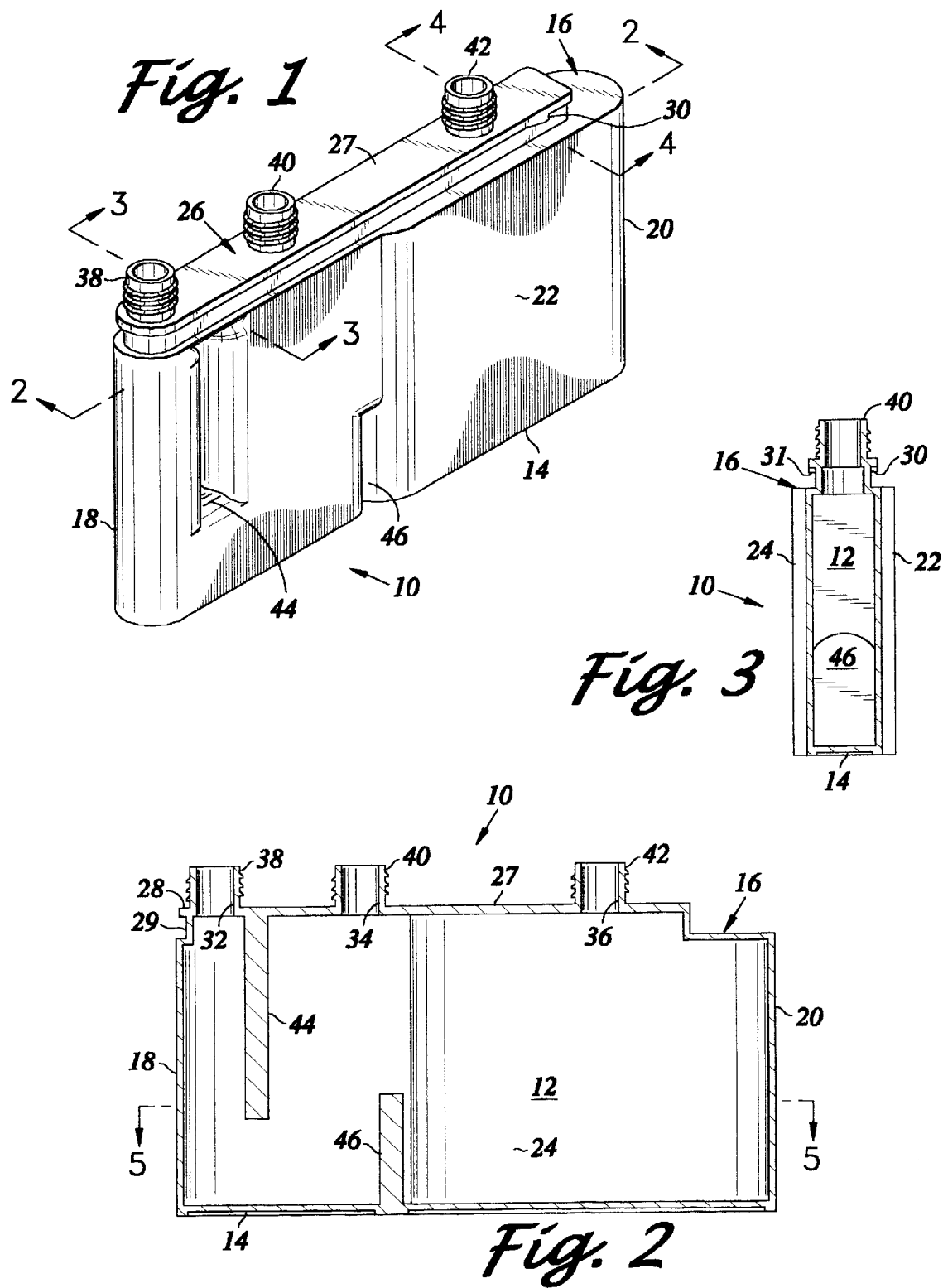

REAGENT CARTRIDGE

FIELD OF INVENTION

The present invention relates to reagent cartridges for use in automated clinical analyzers and, more particularly, to an improved single compartment, non-wedge shaped reagent cartridge.

BACKGROUND

It is common in diagnostic laboratories to utilize automated clinical analyzers for simultaneously or serially analyzing body fluid samples. It is common for such analyzers to include rotatable carrousels for receiving a plurality of reagent cartridges from which different reagents are aspirated and dispensed during the operation of such clinical analyzers.

Representative of such reagent cartridges is the reagent cartridge described and illustrated in U.S. Pat. Nos. 4,970,053 and 5,075,082, which are incorporated herein by reference.

The reagent cartridge described and illustrated in the foregoing patents is wedged shape and includes a plurality of storage compartments. The cartridge includes wall members and connecting members formed integrally with the storage compartments for holding the storage compartments in a fixed relationship with respect to each other while separating the wall members from each other to prevent reagent migration between adjacent reagent compartments. Each reagent storage compartment includes an access opening with a neck formed about the opening and including a collar adapted to accommodate an automatically controlled reagent transfer probe. The reagent cartridge is adapted to be inserted into slots formed in a rotatable carousel of the automated analyzer, the slots together with the collars forming a positioning and detent mechanism for removeably securing the cartridge in the slot of the carousel.

Such reagent cartridges are relatively complex and expensive in structure and manufacture. Accordingly, there is a need for an improved reagent cartridge which does not incorporate the complex and structurally expensive wedge shaped multi-compartment features of the prior reagent cartridge. The present invention satisfies such a need.

SUMMARY OF INVENTION

To satisfy the foregoing need, the present invention comprises a non-wedge shaped reagent cartridge comprising a single hollow, relatively narrow, axially elongated reagent compartment. The reagent compartment comprises an elongated axially extended bottom member and an elongated axially extending top member. Front and rear end portion extend vertically between the top and bottom with opposing right and left sidewalls extending vertically between the top and bottom and connected to the front and rear portions to complete the reagent compartment. A shoulder engaging flange extends from the top of the reagent compartment. It is the function of the flange to support the reagent cartridge on a shoulder located within a rotatable carousel of an automated clinical analyzer. The reagent cartridge further includes at least one opening in the top of the reagent compartment for receiving a fluid transfer probe of an automated clinical analyzer into which the reagent cartridge is inserted.

BRIEF DESCRIPTION OF DRAWINGS

FIG. 1 is a perspective view of a preferred embodiment of a reagent cartridge of the present invention.

FIG. 2 is a sectional side view of the reagent cartridge along the line 2—2 in FIG. 1.

FIG. 3 is a sectional front view of a reagent cartridge along the line 3—3 in FIG. 1.

DETAILED DESCRIPTION OF INVENTION

Figure 4:
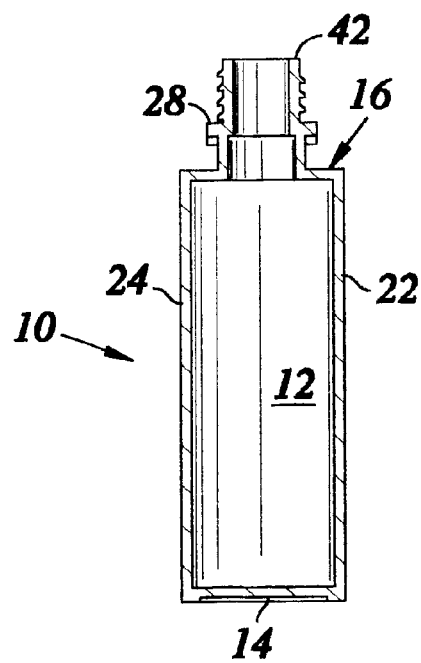
FIG. 4 is a sectional front view of the reagent cartridge along the line 4—4 in FIG. 1.
Figure 5:
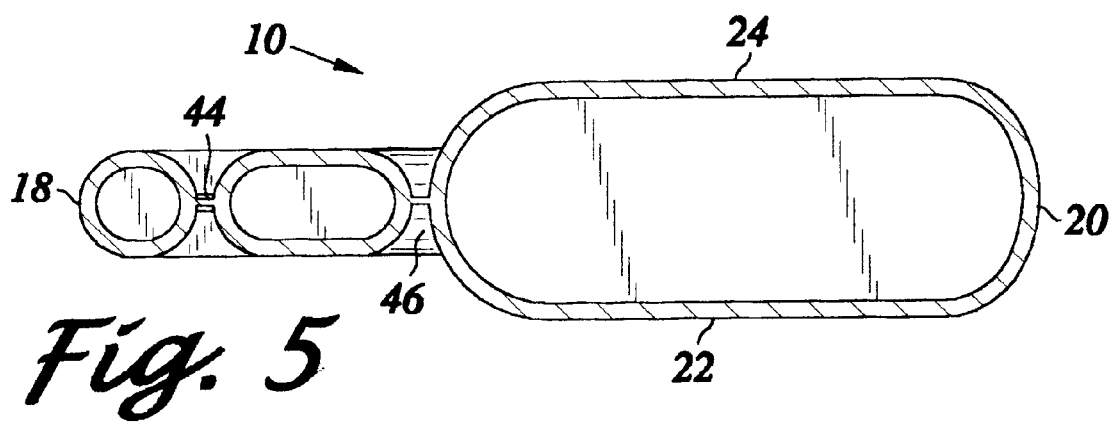
FIG. 5 is a sectional top view of the reagent cartridge along the line 5—5 in FIG. 2.

Basically, as illustrated in FIG. 1, the present invention comprises a non-wedge shaped reagent cartridge 10 forming a single hollow, relatively narrow axially elongated reagent compartment 12. The reagent compartment 12 is formed from and comprises an axially elongated horizontally extending bottom 14 and an axially elongated top 16. Slightly concave front and rear portions 18 and 20 extend vertically from the bottom 14 to the top 16. Opposing right and left sidewalls 22 and 24 also extend vertically from the bottom 14 to the top 16 and connect to the front and rear portions 18 and 20 to complete the axially elongated reagent compartment 12.

As illustrated, the top 16 includes a raised upper region 26 extending from adjacent the front end portion 18 to a location adjacent the rear end portion 20. The raised upper region 26 includes a flat axially elongated top surface 27 and a continuous flange 28 extending outwardly from the top surface beyond a lower outer surface 29 of the raised upper region 26. The continuous flange 28 defines a downwardly facing shoulder for engaging and sliding along an upwardly facing shoulder along a slot in a carousel (not shown) in a conventional automated clinical analyzer. Such a carousel is designed in a wheel configuration to radially receive a plurality of reagent cartridges containing liquid reagents for use in the analysis of sample fluids. To index the cartridge 10 within such a carousel, the flange 28 includes downwardly directed teeth 30 and 31 extending from opposite sides of the raised upper region 26 adjacent a rear end of the region. The teeth engage detents or slots in the carousel for securing the reagent cartridge in place during operation of the associated automated clinical analyzer.

To provide access to the reagent contained within the reagent cartridge 10, the reagent cartridge includes one or more openings for receiving fluid transfer probes of the automated clinical analyzer into which the cartridge is inserted. In the illustrated embodiment of the present invention, the cartridge 10 includes three openings 32, 34 and 36 extending through the top 27 of the raised upper region 26 and open into the interior of the reagent compartment 12 as best depicted in FIG. 2. Surrounding each of the openings is a threaded collar here depicted as collars 38, 40 and 42 for the openings 32, 34 and 36 respectively. The collars are adapted to receive threaded caps (not shown) for closing the reagent compartment 12.

When it is desired to utilize the reagent cartridge 10 and to allow an associated automated clinical analyzer to sample the reagents contained in the cartridge, the caps are removed from the threaded collars 38, 40 and 42 and the front end portion 18 of the cartridge 16 is moved into a slot in the rotatable carousel of the automated clinical analyzer with the flange 28 resting on the top shoulder surface along the receiving slot in the carousel as previously described. In operation of the clinical analyzer, fluid transfer probes are inserted into one or more of the openings 32, 34 and 36 through the collars 38, 40 and 42 respectively.

As the fluid transfer probes are inserted into the reagent compartment 12 and secured in place by connecting structure of the associated automated clinical analyzer, the liquid reagent within the compartment 12 is contacted and agitated slightly by the insertion of the probes. Further, as the carousel in which the cartridge 10 is mounted is rotated, the liquid reagent within the cartridge is moved with the rotary motion of the carousel. Such motion is periodically stopped and started causing the liquid reagent to slosh within the compartment 12 with waves being created in the top surface of the reagent. In order to prevent any of the liquid reagent contained in the reagent compartment 12 from splashing out any of the openings 32, 34 or 36 through their associated collars 38, 40 and 42, the preferred embodiment of the present invention incorporates a top baffle 44 illustrated in FIG. 2 as extending downwardly from the top 27 of the raised upper region 26 of the top 16 of the cartridge 10. The baffle 44 extends approximately two thirds of the distance between the top 27 and bottom 14 and prevents the liquid reagent contained in the compartment 12 from splashing out of the opening 32 at the forward end of the cartridge while it is being handled. In the absence of the top baffle 44, quick movement of the cartridge 10 might cause reagent to exit the compartment even though the cartridge 10 is in an upright position. Liquid reagents are expensive and some are caustic. Accordingly, accidental escape of reagents from the cartridge 10 should be and is prevented by the inclusion of the top baffle 42.

Reagent movement within the cartridge 10 can also generate bubbles or small waves which should be eliminated. As previously indicated, during operation of the automated clinical analyzer in which the cartridge 10 is inserted, the cartridge is moved rapidly on the supporting carousel. This motion can cause the reagent to form bubbles and waves. Automated clinical analyzers often include liquid sensing mechanisms to monitor the reagent level. If such mechanisms sense a bubble or the bottom of a wave, the detected level would be in error. If the analyzer senses a low or zero reagent level, the cartridge could be improperly excluded from operation with no test being analyzed for that particular cartridge. To prevent such occurrences, the preferred embodiment of the present invention includes a lower baffle 46. As shown most clearly in FIG. 2, the bottom baffle 46 extends vertically from the bottom 14 between the front and rear openings 32 and 36 and preferably just to the rear of the opening 34. The bottom baffle 46 functions to greatly reduce reagent movement within the compartment 12 thus eliminating the waves/bubble problem previously referred to and insuring continuous operation for the cartridge 10.

The bottom baffle 46 also accommodates differential aspiration between two fluid transfer probes which may enter the cartridge 10 for reagent pickup. In this regard, it is common in automated clinical analyzers that the analyzer be programmed to a known ratio between reagent aspirated by two probes inserted into a cartridge commonly referred to as probe A and probe B. The lower baffle 46 is positioned so that the ratio of reagents on either side of the baffle is consistent with the expected programmed ratio. Without the baffle, the reagent level could drop faster beneath one of the probes than the analyzer expects. In such a case, the reagent probe would assume a programmed level which prevented aspiration of reagent. This of course would be an error condition causing the associated cartridge to be removed from operation. Such erroneous operation is prevented by inclusion of a bottom baffle 46 in the preferred embodiment in the cartridge 10.

The baffles 44 and 46 are formed in the cartridge 10 of the present invention during the molding operation of the cartridge. In this regard, the cartridge 10 is preferably formed by blow molding as opposed to injection molding. In such blow molding, the right and left sidewalls 22 and 24 are drawn inwardly to engage in the region of the baffles 44 and 46 to form the baffles as part of a single piece molded plastic. This is to be contrasted with injecting molding of a cartridge which requires two pieces which must be glued or otherwise welded or secured together. Blow molding is considerably less expensive than ejection molding and further reduces the overall cost of the cartridge of the present invention.

An additional feature of the cartridge 10 is the inclusion of the continuous flange 28. As illustrated and as previously described, the flange is located at the raised upper region 26 of the cartridge and extends from the first opening 32 to the third opening 38. As previously indicated, the function of the flange is to hold the cartridge 10 in position on the reagent carousel of an associated automated analytical analyzer. Being uninterrupted and continuous, the flange 28 eliminates any possibility of jamming of the cartridge in loading. This feature improves the ease of use in handling and loading of the cartridge 10.

While a particularly preferred embodiment of the present invention has been illustrated and described above, changes and modifications may be made in the illustrated embodiment without departing from the spirit of the present invention. Accordingly, the present invention is to be limited in scope only by the terms of the following claims.

I claim:

1. A single compartment, non-wedge shaped reagent cartridge, comprising:
    a hollow axially elongated reagent compartment comprising
        an axially extending bottom,
        an axially extending top,
        a front end portion extending vertically between the bottom and top,
        a rear end portion extending vertically between the bottom and top, and
        opposing right and left side walls extending upward from the bottom to the top and connecting to the front end portion and to the rear end portion;
    a shoulder engaging flange extending from the top for supporting the cartridge on a shoulder in a cartridge receiving carousel of an automated clinical analyzer;
    a baffle extending from the top or bottom into the reagent compartment; and at least one opening in the top for receiving a fluid transfer probe of an automated clinical analyzer.

2. A single compartment, non-wedge shaped reagent cartridge comprising:

a hollow axially elongated reagent compartment comprising
an axially extending bottom,
a closed axially elongated extending top including a vertically raised upper region,
a front end portion extending vertically between the bottom and top,
a rear end portion extending vertically between the bottom and top, and
opposing right and left side walls extending upward from the bottom to the top and connecting to the front end portion and to the rear end portion;
a shoulder engaging flange extending laterally outward from the raised upper region of the top between the front and rear end portions for supporting the cartridge on parallel spaced shoulders in a cartridge receiving carousel of an automated clinical analyzer; and at least one opening in the raised upper region of the top for receiving a fluid transfer probe of the automated clinical analyzer.

3. The reagent cartridge of claim 1 wherein the baffle comprises a top baffle extending vertically from the top into the reagent compartment.

4. The reagent cartridge of claim 3 wherein the top baffle is adjacent the opening.

5. The reagent cartridge of claim 1 wherein the baffle comprises a bottom baffle extending vertically from the bottom into the reagent compartment.

6. The reagent compartment of claim 5 wherein the opening includes first and second top openings in the reagent cartridge and the bottom baffle extends vertically from the bottom at a location between the first and second and top openings.

* * * * *